United States Patent [19]

Noller et al.

[11] Patent Number: 4,867,165
[45] Date of Patent: Sep. 19, 1989

[54] METHOD FOR DETERMINING THE PERFUSION

[75] Inventors: Friedemann Noller, Herrenberg; Klaus Forstner, Tamm, both of Fed. Rep. of Germany

[73] Assignee: Hewlett-Packard Company, Palo Alto, Calif.

[21] Appl. No.: 85,594

[22] Filed: Aug. 13, 1987

[30] Foreign Application Priority Data

Jun. 3, 1987 [DE] Fed. Rep. of Germany ..... 87108024

[51] Int. Cl.$^4$ ................................................ A61B 5/00
[52] U.S. Cl. ..................................... 128/633; 128/666; 356/382
[58] Field of Search ............... 128/633, 694, 666, 774; 356/39, 382, 381

[56] References Cited

U.S. PATENT DOCUMENTS

| | | | |
|---|---|---|---|
| 3,496,373 | 2/1970 | Thorman et al. | 356/382 X |
| 3,545,430 | 12/1970 | Figar | 128/694 |
| 3,732,016 | 5/1973 | Deshayes | 356/382 |
| 4,109,643 | 8/1978 | Bond et al. | 128/666 |
| 4,167,331 | 9/1979 | Nielsen | 356/39 |
| 4,407,290 | 10/1983 | Wilber | 128/633 |

FOREIGN PATENT DOCUMENTS 0008004 1/1987 Japan ..................................... 356/382
WO86/05674 10/1986 World Int. Prop. O. .

OTHER PUBLICATIONS

IEEE Transactions on Biomedical Engineering, BME-33, Aug., No. 8, New York, pp. 795-797: Noninvasive Measurement of the Volume Elastic Modulus in Finger Arteries Using Photoelectric Plethysmography.

Primary Examiner—William E. Wayner
Attorney, Agent, or Firm—Richard Schuette

[57] ABSTRACT

A method is proposed for determining the perfusion by evaluation of the light emitted by at least one light source and influenced by the arterial blood, by use of optical measuring means which measure the intensity variation as a consequence of the variation in arterial blood volume. According to this method, the perfusion is either displayed as variation in thickness from the sum of the parallel tissue enlargements d or as normalized volume. The perfusion is derived by one or more measurements of light intensity. According to the invention, for the first time a method for determining perfusion as a quantitative value is provided.

4 Claims, 4 Drawing Sheets

METHOD FOR DETERMINING THE PERFUSION

BACKGROUND OF THE INVENTION

The pulsation of arterial blood causes a pulsating volume variation of the arteries. If light emitted by a light source is transmitted through a part of the body being supplied with blood, the light is attenuated in dependence on the pulsation. The resulting variation in intensity of the light received by means of a sensor may, for example, be used for the determination of oxygen saturation of blood. The correlation between light absorption in the tissue and the composition and the thickness of the tissue through which the light passes is provided by Lambert-Beer's Law, and detection of scattering effects is provided by its modifications.

U.S. Pat. No. 4,109,643 discloses an apparatus for measuring the perfusion employing a light emitting diode for a measurement in the region of the fingertip. For this purpose, the light emitting diode is mounted on one side of a finger cap, and photo sensitive sensor is mounted on the opposite side. In this known apparatus, a change of the perfusion trend can be detected by means of electronic evaluation means, but no details may be obtained about the percentage volume change of the arterial blood upon a pulsation. As normal perfusion is not available before operations —e.g. caused by a shock condition of the patient, no exact statement may be provided about the condition of the patient during the operation by way of measuring the change in perfusion. A measurement of the change in perfusion is only useful if a correct reference value for the patient could be established before disturbance of perfusion occurred. In addition, measurement of perfusion may physiologically be used as an indication of the stress condition of a patient.

BRIEF DESCRIPTION OF THE INVENTION

In accordance with the present invention means and method are provided for determining the amount of perfusion. The volume variation of the arterial blood is accompanied by various small variations in thickness so that the parts of the equation containing a variation in thickness of higher order may be ignored. Therefore, the approximate result is that the volume variation (referred to the measurement volume) corresponds to approximately three times the thickness variation of the medium total cross-section of the arterial vessels (referred to the thickness of the measurement volume supplied with blood). As light absorption is not only dependent on the volume of the tissue supplied with blood, but also on the concentration of the light-absorbing components of the blood, for example the concentration of hemoglobin or oxihemoglobin, the concentration of these components has to be determined in advance in known manner by measurement of the oxygen saturation so that the perfusion can be determined by light absorption by means for measuring at a single wavelength. There is also the possibility of eliminating oxygen saturation as an unknown quantity arithmetically by multiple measurements using different wavelengths.

By multiple measurements, further parameters of the underlying equation may be determined or eliminated. For example, by measurements at three different wavelengths the hemoglobin concentration, the oxygen saturation and the perfusion can be determined. Alternatively, the hemoglobin concentration may be assumed approximately as 140 g/l~8,7 mMol/l for women and as 160 g/l~9,94 mMol/l for men. In newborns, the hemoglobin concentration is 200 g/l~12,42 mMol/l on an average.

DETAILED DESCRIPTION OF THE INVENTION

Figure 1:
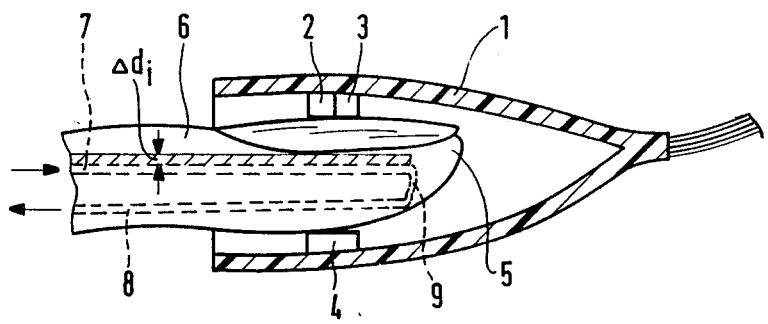
FIG. 1 shows a measurement cap put on a fingertip and comprising two light-emitting diodes and a photo receiver.

According to FIG. 1, a measurement cap 1 comprising two light emitting diodes 2, 3 and a photo receiver 4 is put over a fingertip 5. The arteries 7 and veins 8 running through tissue 6 are indicated schematically by dotted lines. Between arteries 7 and veins 8, capillaries 9 are located. These capillaries have pressure-reducing characteristics so that a pulsation and an associated pulse-dependent volume variation occurs only in the artery 7.

Figure 4:
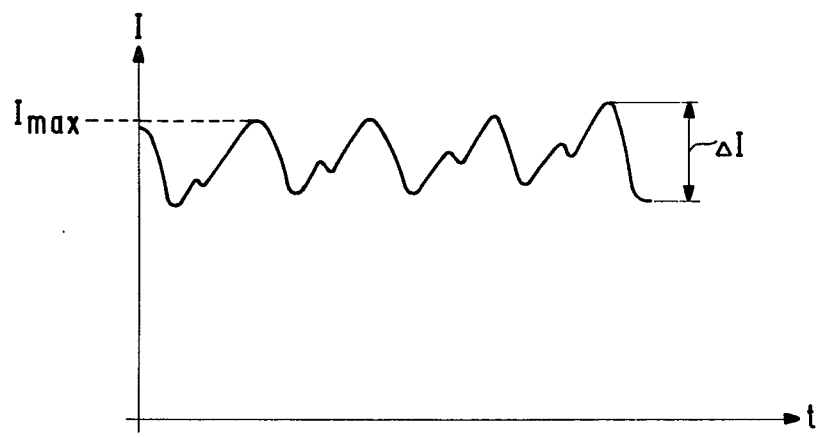
FIG. 4 shows the current variation occurring at the photo receiver and being influenced by the pulsation of the arterial blood.
Figure 6:
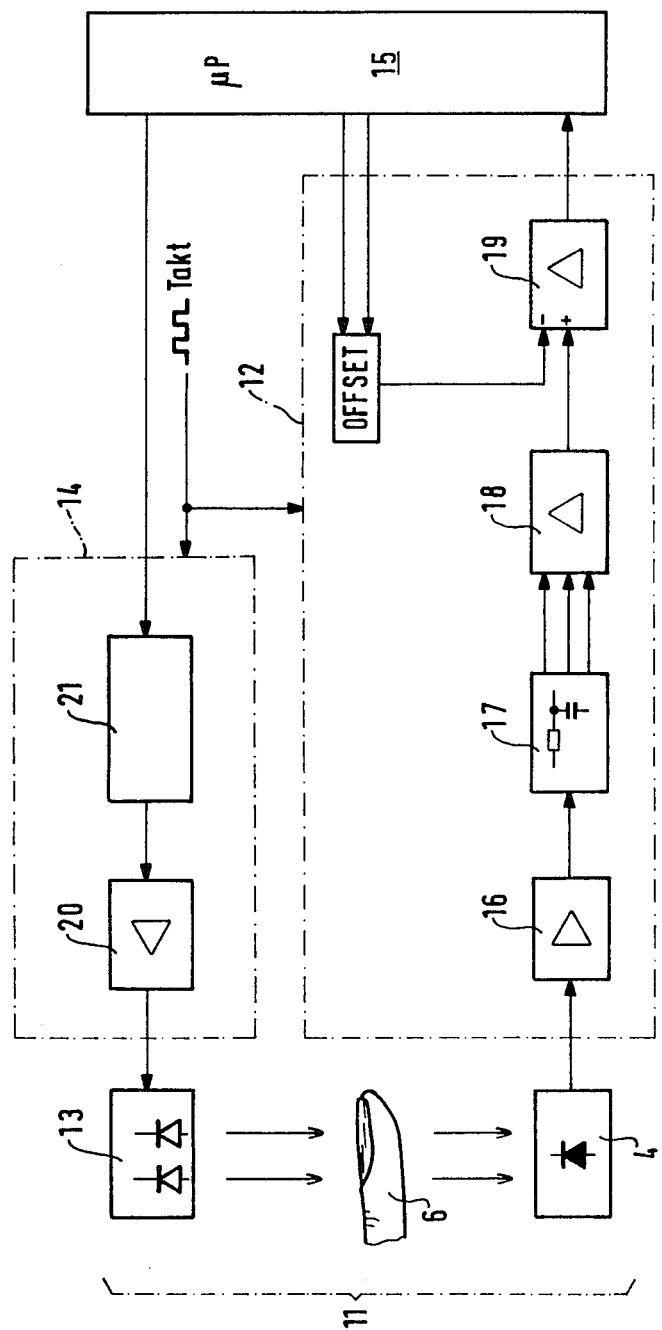
FIG. 6 shows a block diagram of an apparatus for measuring the perfusion.

Light emitting diodes 2, 3 emit light of different wavelengths, e.g. 660 nm and 950 nm, to photo receiver 4. Photo receiver 4 converts the received light into a current signal as illustrated in FIG. 4. The current signal is evaluated by evaluation means as exemplarily shown in FIG. 6 to determine the perfusion.

Figure 2:
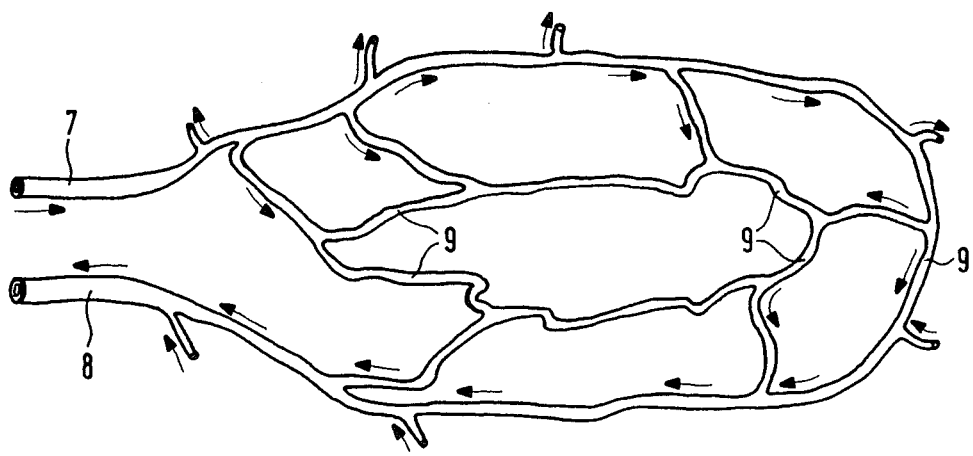
FIG. 2 shows the basic structure of a tissue with arteries and veins running through it.

FIG. 2 shows the structure of a part of tissue supplied with blood. Blood flows in through artery 7 and reaches—via capillaries 9 and cells—vein 8 by means of which vein it flows away.

If a part of tissue supplied with blood is irradiated by a light source, the light is subject to absorption in the tissue, said absorption being dependent—in first approximation—on the molecular extinction coefficient E, the concentration c of the dissolved dye and the thickness d of the transmitted layer.

Figure 3:
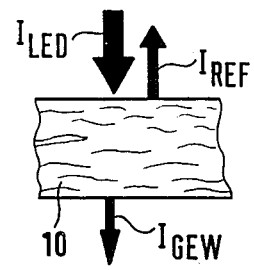
FIG. 3 shows part of a tissue being irradiated with light which partially transmits said tissue and partially is reflected by the same.

FIG. 3 depicts part of a tissue 10 being irradiated by light corresponding to current $I_{LED}$, the tissue thereby causing a reflection or a transmission with the intensity $$I_{GEW} = I_{LED} \times e^{-Ecd} \quad (1),$$

IGEW being the intensity after the absorber at the detector, $I_{LED}$ being the intensity before the or without absorber, E being the molecular extinction coefficient, E (λ) [l /Mol x cm]

c being the molecular concentration of the absorbing substance [Mol/l]

d being the thickness of the absorber [cm]

Equation (1) is Lambert-Beer's Law. For strict validity, parallel monochromatic light with an optically homogenous absorber is required. The real composition of a part of the body supplied with blood (e.g. a fingertip) requires, for example, for the light absorption of the blood that the discrete blood corpuscles be taken into consideration as scattering centers. Therefore, for more accurate reflection, the diffusion of light quantum has to be taken into consideration so that instead of the extinction being a constant quantity it has an effective value of $E_{\text{eff}}(\lambda, C_{Hb}, C_{Hb02}...)$ for given wavelengths. The effective extinction depends on other factors such as the hemoglobin concentration.

For the purpose of simplifying the description, equation (1) is assumed to be valid.

For the overall tissue absorption, the following separation in a time-dependent component and a time-independent component is valid for a part of the body supplied with blood in a pulsating manner, corresponding to the principle of pulse oximetry:

$$E_{cd} = E_{Hb} \times c_{Hb} \times \Delta d(t) + E_{Hb02} \times c_{Hb02} \times \Delta d(t) + E_N \times c_N \times d_N \quad (2)$$

$E_{Hb02} \times c_{Hb02} \times d(t)$ being the time-dependent component of oxihemoglobin, $\Delta d(t)$ is the medium overall cross-sectional enlargement of the arterial vessels, and $E_N \times c_N \times d_N$ is the time-independent absorption of the remaining part of the body.

For the time-independent component of the intensity at the detector in the form of a photo receiver, the following equation is deduced:

$$I_{max} = I_{LED} \times e^{-E_N \times c_N \times d_N} \quad (3)$$

and for the time-dependent, pulsating component:

$$I(t) = I_{max} - I_{GEW} = I_{max}(1 - e^{-(E_{Hb} \times c_{Hb} + E_{Hb02} \times c_{Hb02}) \times \Delta d(t)}) \quad (4)$$

A generalization of equation (4) leads for a blood composition consisting of n optically active components to $$\ln(1 - \Delta I/I_{max}/\lambda i) = -(E_{1i} \times c_1 + E_{2i} \times c_2 + E_{ni} \times c_n)\Delta d \quad (5)$$

$E_{ni}$ being the molecular extinction coefficient of the absorber n upon wavelength$\lambda i$, $c_n$ being the molecular concentration of the absorber n in the pulsating volume, $\Delta d$ being the medium overall cross-sectional enlargement of the arterial vessels.

For small variations in intensity, the following equation is approximately valid:

$$\Delta I/I_{max} \sim \ln(1 - \Delta I/I_{max}) \text{ for } \Delta I << I_{max} \quad (6)$$

i.e $\Delta I/I_{max}$ is in proportion to the medium overall cross-sectional enlargement $\Delta d$ and therefore to the perfusion thickness $\Delta d$.

Corresponding to the number of unknown quantities in equation (5), a set of equations is defineable with the corresponding number of measuring values with wave lengths $\lambda_i$.

In the case of a two-wavelength system, for instance oxygen saturation can be determined as $$S = c_{Hb02}/[Hb], \quad (7)$$

$$[HB] = c_{Hb} + c_{Hb02}$$

being the overall hemoglobin concentration.

As a further quantity, the perfusion thickness $\Delta d$ may be determined. If the hemoglobin concentration can be assumed or is known or can be determined by a third wavelength.

$$d = \frac{(E_{Hb02} - E_{Hb})_1 \times \ln\left(\frac{1 - \Delta I}{I_{max}}\right)_2 (E_{Hb02} - E_{Hb})_2 \times \ln\left(\frac{1 - \Delta I}{I_{max}}\right)_1}{[Hb][E_{Hb02}(2) \times E_{Hb}(1) \times E_{Hb02}(1) \times E_{Hb}(2)]} \quad (8)$$

e.g.:

(1) = wavelength 660 nm (2) = wavelength 950 nm $E_{Hb}(1) = 820$ l/Mol cm $E_{Hb02}(1) = 100$ l/Mol cm $E_{Hb}(2) = 100$ l/Mol cm $E_{Hb02}(2) = 260$ l/Mol cm

[Hb] = 9 mMol/l

If we choose an isobestic point $E_{Hb} = E_{Hb02}$, a single measurement value $\Delta I/I_{max}$ is sufficient to determine the perfusion.

Figure 5:
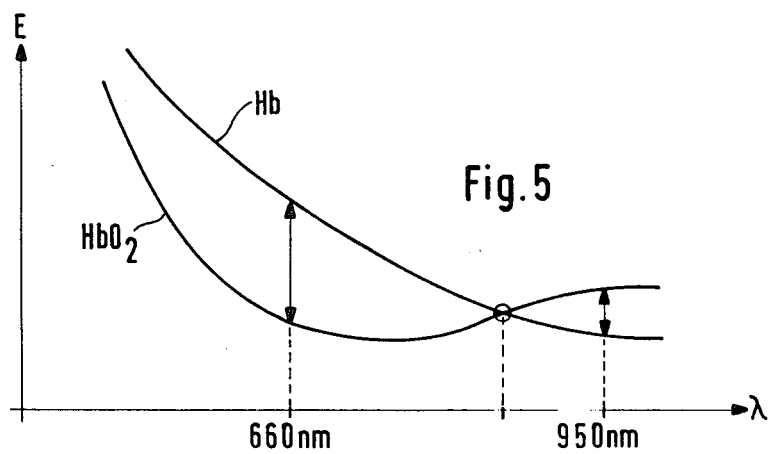
FIG. 5 shows the extinction coefficient for different oxygen saturations in dependence of the wavelength of the irradiated light.

The term "isobestic point" refers to the wavelength at which the extinction coefficient of haemoglobin and un-oxygenated haemoglobin are equal. This point occurs at approximately 800 nm and is illustrated in FIG. 5, as the point of intersection between the oxygenated and un-oxygenated haemoglobin curves.

The measurement values $\Delta I/I_{max}(1) = 0.06$ and $\Delta I/I_{max}(2) = 0.1$ yield for the perfusion thickness $\Delta d = 0.046$ cm.

Another possible definition of the perfusion is the relative volume variation $\Delta V/V$, $\Delta V$ corresponding to the blood volume variation per pulsation and V corresponding to the assigned measurement volume between light source and detector. If the variation in perfusion thickness is $\Delta d \ll d$, d corresponding to the overall absorber thickness (e.g. the finger), we obtain—assuming generally regular enlargement—

$$(V_{max} - V)/V = \Delta V/V \sim 3 \Delta d/d \text{ for } \Delta d \ll d \quad (9)$$

The thickness of a finger is 1 cm on an average; therefore, equation (9) is sufficiently met.

Equation (3) may be used to determine d if $E_N x$ $c_N$ and $I_{LED}$ are known.

Assuming that $I_{LED}(1) = \alpha_1 \times I_0$ and $I_{LED}(2) = \alpha_2 \times I_0$; then $$d_N = \ln\left(\frac{\alpha_1 \times I_{max}(2)}{\alpha_2 \times I_{max}(1)}\right) \frac{1}{E_N \times c_N(1) - E_N \times c_N(2)} \quad (10)$$

The difference, $E_N x \ c_N(1) - E_N x \ c_N(2)$ once determined for a constant absorber thickness $d_N$ remains largely constant for largely homogenous organ composition (e.g. the ear lobe). The same applies to the values $\alpha_1$ and $\alpha_2$ once determined from the current/light intensity characteristics and e.g. determined without absorber.

In the case of a point-like light source, in particular when measuring at the fingertip, we obtain with the light intensities $I_{LED}$ and Imax, respectively, for the distance $d_N$ as a first-order approximation $$d_N = \sqrt{\frac{k \times I_{LED}}{I_{max}}} \quad (11)$$

in which equation k is determined from the current/light intensity characteristics, which once determined can approximately be regarded as a constant.

Using equations (10) and (11), respectively, the thickness d of the part of the body supplied with blood may also be continuously measured. This may also be used as an indication for correct sensor positioning. Finally, the perfusion according to equation (9) may be determined as a normalized value of blood volume variation per pulsation at the corresponding part of the body.

In the above example, $d_N = 1$ cm yields $\Delta V/V = 13.8\%$.

The block diagram (FIG. 6) depicts the optical measuring means 11, the photo receiver 4 of said means being connected with an evaluation circuit 12. By way of an example, light source 13 could be carried out in the form of three light-emitting diodes of different wavelengths, said diodes being operated by an LED-control circuit 14. Evaluation circuit 12 and LED-control circuit 14 are connected with a computer 15 and among each other.

The signal received by photo receiver 4 is fed to a sample and hold circuit 17 via a pre-amplifier 16, the intensities associated to the different wavelengths being temporarily stored in said sample and hold circuit. A consecutive differential circuit 18 provides subtraction of values of darkness to eliminate environmental light. A further circuit 19 provides offset subtraction for the different wavelengths. The signals processed in such a way reach computer 15, said computer determining the normalized perfusion $\Delta V/V$ therefrom.

LED-control circuit 14 contains in particular driver circuits 20 associated with the various light emitting diodes of light source 13 and being controlled by a first stage circuit 21 which is controlled by computer 15. A central clock circuit (not explicitly shown in FIG. 6) provides clock-synchronous operation of controlling and evaluation.

Figure 7:
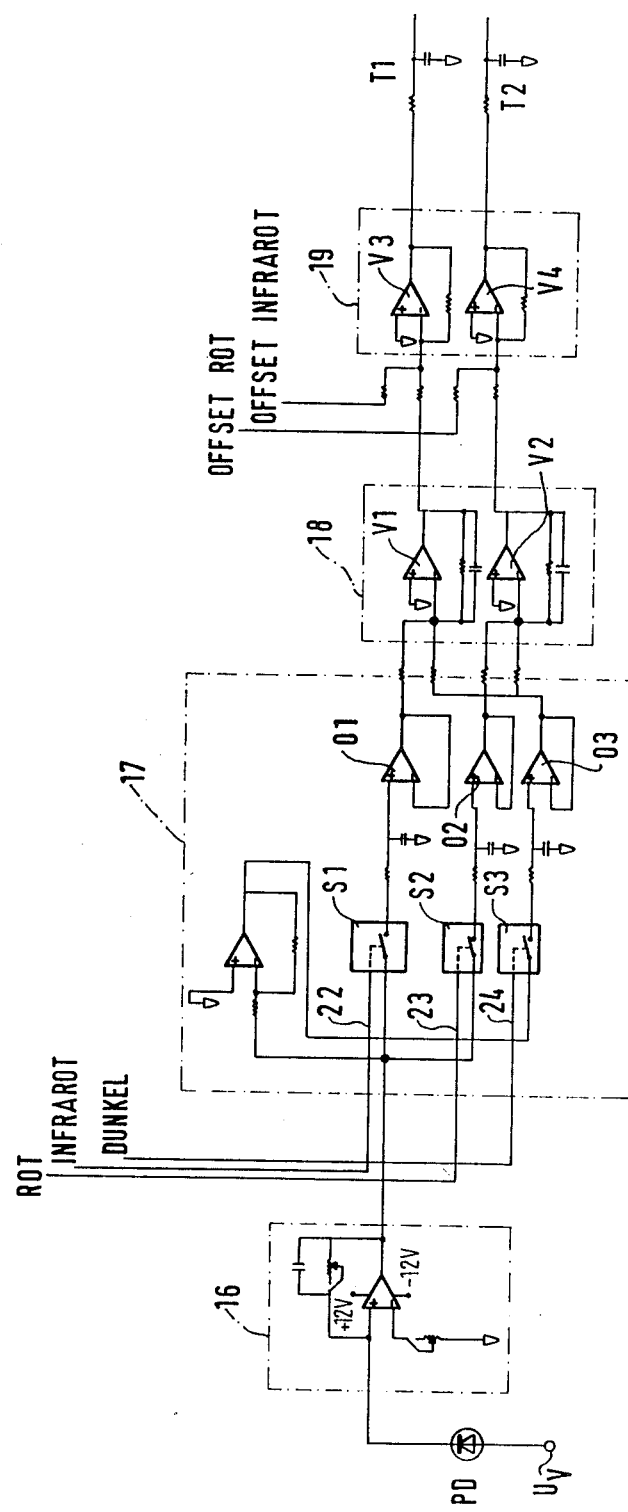
FIG. 7 shows the analogous receiver electronics for the optical measurement apparatus used in FIG. 6.

The part shown in FIG. 7 depicts evaluation circuit 12 in detail. A photo diode PD serves as photo receiver 4, said photo diode being operated with a bias voltage $U_V$. The signal of the photo diode is fed to switches S1 to S3 via pre-amplifier 16, said switches being operated at their control inputs 22 to 2 by the LED-control circuit. Switches S1 to S3 are connected with the positive inputs of three operational amplifiers 01 to 03. Circuit 18—used for the subtraction of the value of darkness—contains two differential amplifiers V1, V2, the outputs of these differential amplifiers being connected with further differential amplifiers V3, V4 of circuit 19. The evaluation circuit is connected with computer 15 via low-pass filters T1, T2.

The method according to the invention is not only suited for the determination of perfusion, but it can—for example—also be used as a stress indicator or for the indication of the sensor positions.

We Claim:

1. A method for determining the perfusion of blood in a body member comprising:
    passing light having the isobestic wavelength through a member of the body,
    measuring the variation, in intensity, $\Delta I$, of light emerging from said body member due to arterial blood volume variation, and
    deriving from $\Delta I$ one of the variations in thickness, $\Delta d/d$, of the body member or the variation in volume $\Delta V/V$.

2. A method according to claim 1 wherein the light intensity variation ($\Delta I$) is converted into a current variation by optoelectronic means and is determined as relative variation in current ($\Delta I/Imax$), and that the perfusion thickness $\Delta d$ or the normalized perfusion $\Delta V/V$ is determined by a substitution of the known determined quantities in:

$$d = \frac{-\ln\left(1 - \frac{I}{I_{max}}\bigg|\lambda_i\right)}{(E_{1i} \times c_1 + E_{2i} \times c_2 + \ldots + E_{ni} \times c_n)}$$

$\Delta I/Imax$ being the relative variation in intensity at the isobestic wavelength $\lambda_i$, $c_1$ to $c_n$ being the molecular concentrations of hemoglobin, oxihemoglobin or other substances,
    $E_{1i}$ to $E_{ni}$ being the extinction coefficients for hemoglobin, oxihemoglobin or other substances at wavelength $\lambda_i$.

3. A method according to claim 2 characterized in that measurements of the relative intensity variation ($\Delta I/Imax$) are carried out at a number of different wavelengths and that these measurements are used to determine a corresponding number of unknown equation parameters such as hemoglobin concentration, oxygen saturation and perfusion.

4. A method for determining the perfusion of blood in a body member comprising:
    passing light, of two different wavelengths which both differ from the isobestic wavelength, through a member of the body;
    measuring the variation in intensity, $\Delta I$, of light emerging from said body member due to arterial blood volume variation; and
    deriving from $\Delta I$ one of the variations in thickness, $\Delta d/d$, of the body member or the variation in volume $\Delta V/V$.

* * * * *